(12) United States Patent
Nam et al.

(10) Patent No.: US 11,553,699 B2
(45) Date of Patent: Jan. 17, 2023

(54) **METHOD FOR ALLEVIATING PHENOTYPE OF DEGENERATIVE DISEASE *DROSOPHILA* MODEL BY USING LOW-DOSE RADIATION**

(71) Applicant: KOREA HYDRO & NUCLEAR POWER CO., LTD., Gyeongsangbuk-do (KR)

(72) Inventors: Seonyoung Nam, Seoul (KR); Soojin Hwang, Seoul (KR); Haemin Jeong, Gyeonggi-do (KR)

(73) Assignee: Korea Hydro & Nuclear Power Co., LTD., Gyeongsangbuk-do (KR)

( * ) Notice: Subject to any disclaimer, the term of this patent is extended or adjusted under 35 U.S.C. 154(b) by 917 days.

(21) Appl. No.: 16/461,089

(22) PCT Filed: Nov. 16, 2017

(86) PCT No.: PCT/KR2017/013008
§ 371 (c)(1),
(2) Date: May 15, 2019

(87) PCT Pub. No.: WO2018/093166
PCT Pub. Date: May 24, 2018

(65) Prior Publication Data
US 2020/0053994 A1    Feb. 20, 2020

(30) Foreign Application Priority Data
Nov. 16, 2016   (KR) .................. 10-2016-0152491

(51) Int. Cl.
*A01K 67/033*     (2006.01)
*A61P 25/28*      (2006.01)
*A61N 5/10*       (2006.01)

(52) U.S. Cl.
CPC ............ *A01K 67/0339* (2013.01); *A61N 5/10* (2013.01); *A61P 25/28* (2018.01)

(58) Field of Classification Search
None
See application file for complete search history.

(56) References Cited

U.S. PATENT DOCUMENTS

2005/0241010 A1   10/2005 Greenspan et al.
2015/0140009 A1   5/2015  Goukassian

FOREIGN PATENT DOCUMENTS

KR    1020120032171 A    5/2012
WO       2011035314 A2    3/2011

OTHER PUBLICATIONS

Lenz et al, Journal of Neurochemistry, vol. 127, pp. 453-460 (Year: 2013).*
Fernandez-Funez, P. et al., Modeling the Complex Pathology of Alzheimer's Disease in *Drosophila*, Experimental Neurology, May 27, 2015, pp. 58-71.
Hwang, S. et al., Low-Dose Ionizing Radiation Alleviates Aβ42-inducsed Cell Death via Regulating AKT and p38 Pathways in *Drosophila* Alzheimer's Disease Models, Biology Open, 2019.
Lee, S. et al., The calcineurin inhibitor Sarah (Nebula) exacerbates Aβ42 phenotypes in a *Drosophila* model of Alzheimer's disease, The Company of Biologists Ltd, 2016, pp. 295-306.
Lee, S. et al., Effects of Low-Dose Radiation on *Drosophila melanogaster* Model of Alzheimer's Disease Through Antioxidant Enzymes and Glucose Metabolism, Korean Society for Radiation Protection, 2015 Spring Conference Summary.
Hong, Y. et al., Inhibition of JNK/dFOXO pathway and caspases rescues neurological impairments in *Drosophila* Alzheimer's disease model, Biochemical and Biophysical Research Communications, Jan. 31, 2012, pp. 49-53.
Ijima, K. et al., Dissecting the pathological effects of human Aβ40 and Aβ42 in *Drosophila* : A potential model for Alzheimer's disease, PNAS, Apr. 27, 2004, pp. 6623-6628, vol. 101, No. 17.
Lee, S. et al., The calcineurin inhibitor Sarah (Nebula) exacerbates Aβ342 phenotypes in a *Drosophila* model of Alzheimer's disease, The Company of Biologists Ltd, 2016, pp. 295-306.
Park, S. et al., Suppresive Effects of SuHeXiang Wan on Amyloid-β42-Induced Extracellular Signal-Regulated Kinase Hyperactivation and Glial Cell Proliferation in a Transgenic *Drosophila* Model of Alzheimer's Disease, Biol. Pharm. Bull., 2013, pp. 390-398, vol. 36, No. 3.
Lee, S. et al., Effects of Low-Dose Radiation on *Drosophila melanogaster* Model of Alzheimer's Disease Through Antioxidant Enzymes and Glucose Metabolism, Korean Society for Radiation Protection, 2015 Spring Conference Summary, (2015).
Crowther, D. et al., Intraneuronal Aβ, Non-Amyloid Aggregates and Neurodegeneration in a *Drosophila* Model of Alzheimer's Disease, Neuroscience 132, 2005, pp. 123-135.
Finelli, A. et al., A model for studying Alzheimer's Aβ42-induced toxicity in *Drosophila melanogaster*, Mol. Cell. Neurosci., 2004, pp. 365-375.
Lowe, X. et al., Early Brain Response to Low-Dose Radiation Exposure Involves Molecular Networks and Pathways Associated with Cognitive Functions, Advanced Aging and Alzheimer's Disease, Radiation Research, Feb. 2009.
Wang, B. et al., Total-body low-dose irradiation of mice induces neither learning disability and memory impairment in Morris water maze test nor Alzheimer's disease-like pathogensis in the brain, Journal of Radiation Research, 2014, pp. i20-i21.
Wei, L. et al., Low-Dose Radiation Stimulates Wnt/β-Catenin Signaling, Neural Stem Cell Proliferation and Neurogenesis of the Mouse Hippocampus in vitro and in vivo, Current Alzheimer Research, 2012, pp. 278-289.

* cited by examiner

*Primary Examiner* — Zinna Northington Davis
(74) *Attorney, Agent, or Firm* — Standley Law Group LLP; James L. Kwak; Stephen L. Grant

(57) ABSTRACT

The present invention relates to a degenerative disease model *Drosophila*. More particularly, a technique is disclosed for alleviating the phenotypes of a degenerative disorder symptom of *Drosophila*. Using this technique, illumination with low dose radiation on a degenerative disease model *Drosophila* alleviates symptoms of the degenerative disease.

6 Claims, 2 Drawing Sheets

METHOD FOR ALLEVIATING PHENOTYPE OF DEGENERATIVE DISEASE *DROSOPHILA* MODEL BY USING LOW-DOSE RADIATION

TECHNICAL FIELD

The present invention relates to a degenerative disease *Drosophila* model, and more particularly to a technique for alleviating the phenotypes of a degenerative disease of *Drosophila*.

BACKGROUND ART

Alzheimer's disease is the disease with the highest rate of incidence among neurodegenerative diseases, and thorough research is ongoing into onset mechanisms of Alzheimer's disease and therapies therefor, but complete treatment thereof is still impossible.

Alzheimer's disease is well known as a neurodegenerative disease caused by blocking neurotransmissions due to accumulation, in the brain, of amyloid beta 42 (Aβ42) protein abnormally produced in vivo.

Currently, methods of treating Alzheimer's disease mainly include administration of drugs for inhibiting the accumulation of Aβ42, but have a long administration period and merely decrease the rate of progression of degenerative disease, rather than provide a cure. Recently, radiation therapy has emerged as new neurological therapeutic methods for treating Alzheimer's disease, and low-dose radiation has already been actively used for cancer treatment.

However, there is currently controversy about the therapeutic effect of low-dose radiation on Alzheimer's disease. Although there are prior studies that suggest the therapeutic effect of low-dose radiation on Alzheimer's disease through a mouse model (Wei et al., 2012, Curr. Alzheimer Res.; Lowe et al., 2009, Radiat. Res.), only a series of gene groups is checked, and the effect of alleviating symptoms has not been verified. On the contrary, the scientific basis for proving the therapeutic effect on Alzheimer's disease using low-dose radiation of 100 mSv or less is insufficient, as reported in a paper (Wang et al., Journal of Radiation research, 2014) that suggests that there is no therapeutic effect of radiation. Therefore, it is necessary to construct an in-vivo model that is able to test the therapeutic effect of low-dose radiation before clinical study.

*Drosophila* is well established as an in-vivo model for Alzheimer's disease, and may induce tissue-specific overexpression of Aβ42, a representative protein of Alzheimer's disease pathology, in neurons and eyes via elav-GAL4 and GMR-GAL4, respectively, using the UAS-GAL4 system, and has been used as an in-vivo model in place of humans in studies on the onset mechanism of Alzheimer's disease and the therapeutic effect thereon (Ijima et al., 2004, PNAS; Hong et al., 2012, BBRC; Lee et al., 2016, Dis Model Mech; Park et al., 2013 Biol Pharm Bull).

SUMMARY

Technical Problem

An objective of the present invention is to provide a method of alleviating the phenotypes of a degenerative disease *Drosophila* model.

In addition, an objective of the present invention is to provide a degenerative disease *Drosophila* model, in which the phenotypes of a degenerative disease are alleviated.

In addition, an objective of the present invention is to provide a therapeutic method through exposure to low-dose radiation as therapeutic methods for treating a neurodegenerative disease using a degenerative disease *Drosophila* model.

Technical Solution

In order to accomplish the above objectives, the present invention provides a method of alleviating the phenotypes of a degenerative disease of *Drosophila* using low-dose radiation, the method comprising collecting a *Drosophila* embryo and treating low-dose radiation to the *Drosophila* embryo.

Here, *Drosophila* may be an Alzheimer's disease *Drosophila* model. Also, the Alzheimer's disease *Drosophila* model may be GMIR>Aβ42 or elav>Aβ42.

The low-dose radiation may be applied so that a cumulative dose thereof is 0.05 to 0.1 Gy.

The degenerative disease may be Alzheimer's disease.

The phenotypes of the neurodegenerative disease may be decreased climbing ability or the induction of apoptosis.

In addition, the present invention provides a degenerative disease *Drosophila* model, in which the phenotypes of a degenerative disease are alleviated by treating low-dose radiation to a *Drosophila* embryo.

Advantageous Effects

According to the present invention, a method of alleviating the phenotypes of a degenerative disease by treating low-dose radiation to a degenerative disease *Drosophila* model can be provided.

Also, a degenerative disease *Drosophila* model in which the phenotypes of a degenerative disease are alleviated by treating low-dose radiation to a degenerative disease *Drosophila* model can be provided.

Also, a degenerative disease *Drosophila* model can be analyzed with regard to apoptosis and climbing ability using low-dose radiation, and thereby can be used as a more advanced in-vivo model than a conventional *Drosophila* model, which enables confirmation only through genetic differences.

Also, the present invention suggests an appropriate dose for alleviating phenotypes such as decreased climbing ability and induction of apoptosis in the degenerative disease *Drosophila* model and can thus be used as a basis for the therapeutic effect of low-dose radiation.

Also, the present invention is effective in providing an in-vivo model system that is useful in verifying the therapeutic effect of low-dose radiation before clinical study, as methods for treating Alzheimer's disease among degenerative diseases.

DETAILED DESCRIPTION OF THE EMBODIMENTS

Figure 1:
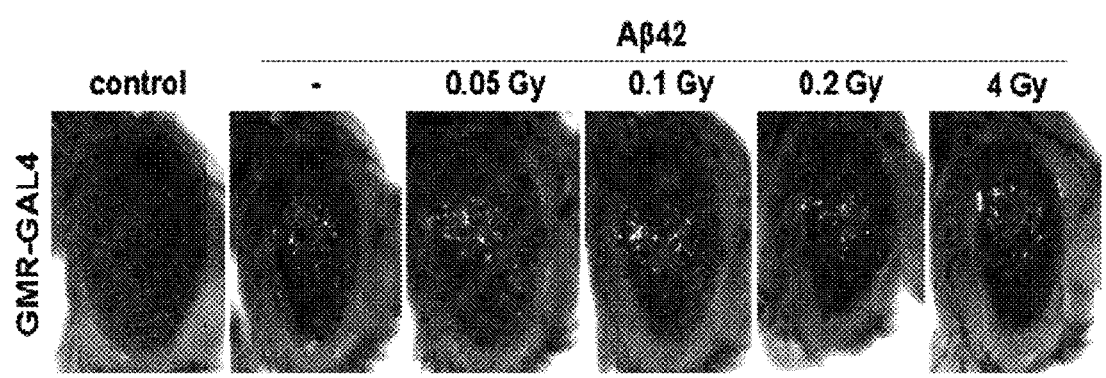
FIG. 1 shows the effect of alleviating the rough eye phenotypem of an Alzheimer's disease *Drosophila* model (GMR>Aβ42) using low-dose radiation.

Hereinafter, a detailed description will be given of the present invention.

An embodiment of the present invention pertains to a method of alleviating the phenotypes of a degenerative disease of Drosophila using low-dose radiation, the method comprising collecting a Drosophila embryo and treating low-dose radiation to the Drosophila embryo.

Here, Drosophila is an Alzheimer's disease Drosophila model. The Alzheimer's disease Drosophila model is GMR>Aβ42 or elav>Aβ42. GMR>Aβ42 and elav>Aβ42 are Alzheimer's disease Drosophila models and are Drosophila models able to induce tissue-specific overexpression of Aβ42, a representative protein of Alzheimer's disease pathology, in the neurons and eyes using the UAS-GAL4 system.

The low-dose radiation is preferably applied so that the cumulative dose thereof is 0.05 to 0.1 Gy ($^{137}$Cs, 0.8 Gy/min), and more preferably 0.05 Gy.

The degenerative disease is Alzheimer's disease. Alzheimer's disease is one of the main causes of senile dementia. The cause of Alzheimer's disease has been found to be highly associated with beta-amyloid protein. When beta amyloid is excessively produced in the body and accumulates in the brain, the function of the neurons deteriorates and thus Alzheimer's disease develops. Beta amyloid paralyzes or deteriorates the function of mitochondria in the neurons, thereby increasing the amount of reactive oxygen species released from the mitochondria. The reactive oxygen species increased makes a fatal wound on intracellular protein or DNA, which in turn results in damage or apoptosis of neurons in brain.

The phenotypes of the degenerative disease include decreased climbing ability and induction of apoptosis.

Another embodiment of the present invention pertains to a neurodegenerative disease Drosophila model, in which the phenotypes of the degenerative disease are alleviated by treating low-dose radiation to a Drosophila embryo.

Here, Drosophila is an Alzheimer's disease Drosophila model. Also, the Alzheimer's disease Drosophila model is GMR>Aβ42 or elav>Aβ42.

The low-dose radiation is preferably applied so that a cumulative dose thereof is 0.05 to 0.1 Gy ($^{137}$Cs, 0.8 Gy/min), and more preferably 0.05 Gy.

The degenerative disease is Alzheimer's disease.

The phenotypes of the neurodegenerative disease include decreased climbing ability and induction of apoptosis.

A better understanding of the present invention will be given through the following examples. These examples are merely set forth to illustrate the present invention but are not to be construed as limiting the scope of the present invention, as is apparent to those skilled in the art.

EXAMPLE 1

Evaluation of effect of alleviating rough eye phenotype of Alzheimer's disease Drosophila model (GMR>Aβ42) using low-dose radiation In order to evaluate the effect of alleviating the phenotype of Alzheimer's disease using low-dose radiation, an Alzheimer's disease Drosophila model (GMR>Aβ42) (Crowther et al., 2003, Neuroscience; Finelli et al., 2004, Mol. Cell. Neurosci.), exhibiting a rough eye phenotype by overexpressing Aβ42, a causative protein of Alzheimer's disease, specifically in the eyes through GMR-GAL4, was used. As a control, Drosophila having only GMR-GAL4 was used, and all Drosophila samples were cultured in an incubator at a temperature of 25° C. and a humidity of 60%.

Respective embryos were collected from control Drosophila (GMR-GAL4) and Alzheimer's disease Drosophila model (GMR>Aβ42) for 6 hr. To evaluate the phenotype alleviation effect of cumulative doses, the embryos of the Alzheimer's disease Drosophila model (GMR>Aβ42) were divided into five groups, four groups of which were irradiated respectively at doses of 0.05 Gy, 0.1 Gy, 0.2 Gy, and 4 Gy ($^{137}$Cs, 0.8 Gy/min). After irradiation of the low-dose radiation, these embryos were grown in an incubator until adulthood, and the eyes of individual adult Drosophila groups were observed using a microscope.

The Drosophila eye microscopy images for confirming the effect of alleviating the rough eye phenotype of the Alzheimer's disease Drosophila model (GMR>Aβ42) using low-dose radiation are shown in FIG. 1. Based on this result, the rough eye phenotype of the Alzheimer's disease Drosophila model (GMR>Aβ42) was confirmed to be alleviated at cumulative doses of 0.05 Gy and 0.1 Gy, and the phenotype alleviation effect was insignificant at 0.2 Gy.

EXAMPLE 2

Evaluation of effect of reducing apoptosis of Alzheimer's disease Drosophila model (GMR>Aβ42) using low-dose radiation Respective embryos were collected from control Drosophila (GMR-GAL) and the Alzheimer's disease Drosophila model (GMR>Aβ42) for 6 hr in the same manner as in Example 1. The embryos of the Alzheimer's disease Drosophila model (GMR>Aβ42) were divided into three groups, two groups of which were irradiated respectively at doses of 0.05 Gy and 4 Gy ($^{137}$Cs, 0.8 Gy/min). After irradiation of the low-dose radiation, the embryos were grown in an incubator until they became $3^{rd}$ instar larvae, and the larval eye discs were dissected, stained with acridine orange (AO), and then observed with a fluorescence microscope.

Figure 2:
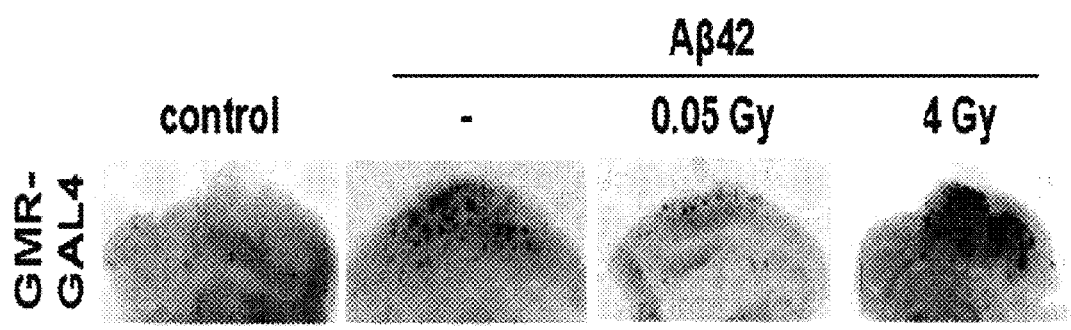
FIG. 2 shows the effect of reducing apoptosis of the Alzheimer's disease *Drosophila* model (GMR>Aβ42) using low-dose radiation.

The results of observation with a fluorescence microscope for confirming the effect of reducing the apoptosis of Alzheimer's disease Drosophila model (GMR>Aβ42) using low-dose radiation are shown in FIG. 2. Based on this result, apoptosis (the portion stained black in FIG. 2), known to be induced due to overexpression of Aβ42 in the Alzheimer's disease Drosophila model (GMR>Aβ42), was confirmed to be reduced by low-dose radiation of 0.05 Gy, whereas high-dose radiation of 4 Gy was found to increase apoptosis.

EXAMPLE 3

Evaluation of effect of alleviating decreased climbing ability phenotype of Alzheimer's disease Drosophila model (elav-Aβ42) using low-dose radiation In order to evaluate the effect of alleviating the phenotype of Alzheimer's disease using low-dose radiation, an Alzheimer's disease Drosophila model (elav>Aβ42), exhibiting a decreased climbing ability phenotype through overexpression of the Aβ42 protein specifically in neurons through elav-GAL4, was used. As a control, Drosophila having only elav-GAL4 was used, and all Drosophila samples were cultured under incubation conditions of a temperature of 25° C. and a humidity of 60%.

Respective embryos were collected from control *Drosophila* (elav-GAL4) and the Alzheimer's disease *Drosophila* model (elav>Aβ42) for 6 hr. The embryos of the Alzheimer's disease *Drosophila* model (elav>Aβ42) were divided into three groups, two groups of which were irradiated respectively at cumulative doses of 0.05 Gy and 4 Gy ($^{137}$Cs, 0.8 Gy/min). After irradiation of the low-dose radiation, these embryos were grown in an incubator until adulthood, and male *Drosophila* samples were collected on the third day of adulthood, and the climbing ability of *Drosophila* groups was tested. The climbing ability test was performed in the same manner as in Hwang et al., (2013) PLoS Genetics.

Figure 3:
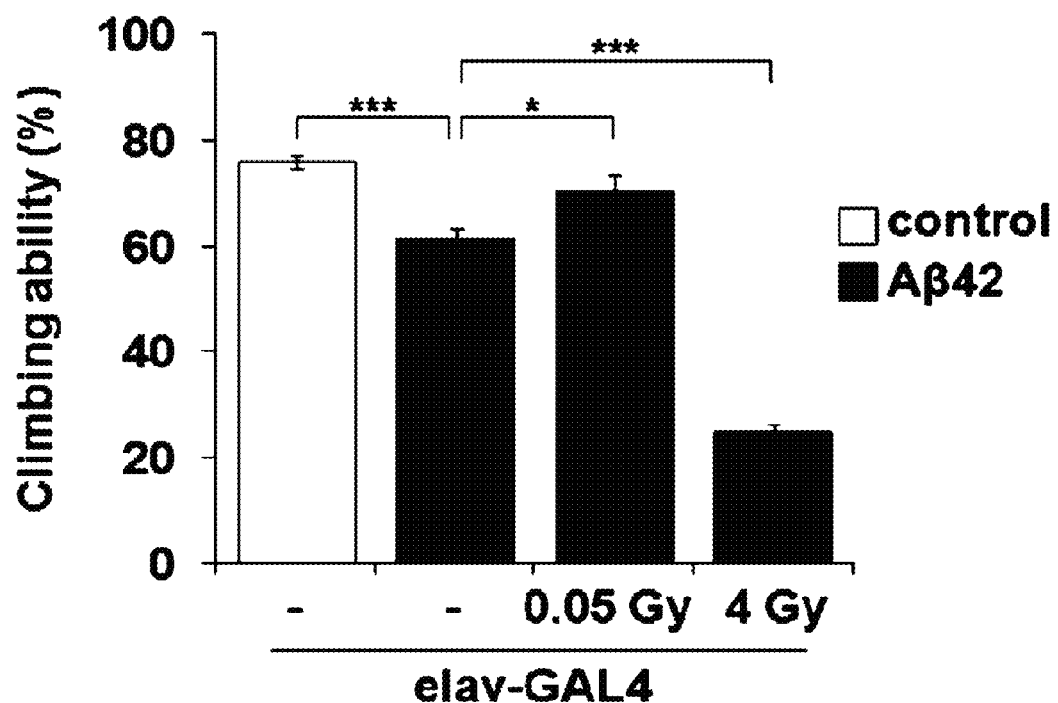
FIG. 3 shows the effect of alleviating the decreased climbing ability phenotype of an Alzheimer's disease *Drosophila* model (elav>Aβ42) using low-dose radiation.

The results of evaluation of the effect of alleviating the decreased climbing ability phenotype of the Alzheimer's disease *Drosophila* model (elav>Aβ42) using low-dose radiation are shown in FIG. 3. Based on this result, the climbing ability was improved in the Alzheimer's disease *Drosophila* model (elav>Aβ42) at a cumulative dose of 0.05 Gy, and was significantly degraded by high-dose radiation of 4 Gy.

EXAMPLE 4

Evaluation of effect of reducing apoptosis of Alzheimer's disease *Drosophila* model (elav>Aβ42) using low-dose radiation Respective embryos were collected from control *Drosophila* (elav-GAL4) and the Alzheimer's disease *Drosophila* model (elav>Aβ42) for 6 hr in the same manner as in Example 3, and the embryos of the Alzheimer's disease *Drosophila* model (elav>Aβ42) were divided into three groups, two groups of which were irradiated respectively at cumulative doses of 0.05 Gy and 4 Gy ($^{137}$Gy, 0.8 Gy/min). After irradiation of the low-dose radiation, the embryos were grown in an incubator until they became larvae, and the brains of the larvae were dissected, stained with acridine orange (AO), and then observed with a fluorescence microscope.

Figure 4:
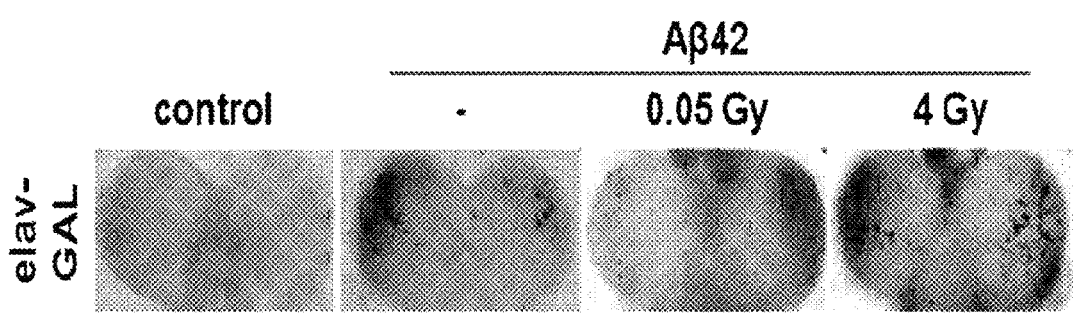
FIG. 4 shows the effect of reducing apoptosis of the Alzheimer's disease Drosophila model (elav>Aβ42) using low-dose radiation.

The results of observation with a fluorescence microscope for confirming the effect of reducing apoptosis of the Alzheimer's disease *Drosophila* model (elav>Aβ42) using low-dose radiation are shown in FIG. 4. Based on this result, apoptosis (the portion stained black in the image) induced due to overexpression of Aβ42 in the Alzheimer's disease *Drosophila* model (elav>Aβ42) was confirmed to be reduced by low-dose radiation of 0.05 Gy, and high-dose radiation of 4 Gy was found to further induce apoptosis.

Although specific embodiments of the present invention have been disclosed in detail as described above, it will be obvious to those skilled in the art that such description is merely of preferable exemplary embodiments and is not to be construed to limit the scope of the present invention. Therefore, the substantial scope of the present invention will be defined by the appended claims and equivalents thereof.

The invention claimed is:

1. A method of alleviating a phenotype of an Alzheimer's disease *Drosophila* model, the method comprising applying low-dose radiation, at 0.05 Gy, to a *Drosophila* embryo, wherein the Alzheimer's disease *Drosophila* model is GMR>Aβ42.

2. The method of claim 1, wherein the phenotype of the Alzheimer's disease is decreased mobility.

3. The method of claim 1, wherein the phenotype of the Alzheimer's disease is induction of apoptosis.

4. A method of alleviating a phenotype of an Alzheimer's disease *Drosophila* model, the method comprising:
applying low-dose radiation, at 0.05 Gy, to a *Drosophila* embryo, wherein the Alzheimer's disease *Drosophila* model is elav>Aβ42.

5. The method of claim 4, wherein the phenotype of the Alzheimer's disease is a decreased mobility or induction of apoptosis.

6. The method of claim 1, wherein the phenotype of the Alzheimer's disease is induction of apoptosis.

\* \* \* \* \*

UNITED STATES PATENT AND TRADEMARK OFFICE
CERTIFICATE OF CORRECTION

PATENT NO. : 11,553,699 B2
APPLICATION NO. : 16/461089
DATED : January 17, 2023
INVENTOR(S) : Seonyoung Nam et al.

It is certified that error appears in the above-identified patent and that said Letters Patent is hereby corrected as shown below:

On the Title Page

References Cited, item (56) Other Publications, please delete "Lee, S. et al., Effects of Low-Dose Radiation on Drosophila melanogaster Model of Alzheimer's Disease Throught Antioxidant Enzymes and Glucose Metabolism, Koren Society of Radiation protection, 2015 Spring Conferens Summary."

References Cited, item (56) Other Publications, please delete "Lee, S. et al., The calcineurin inhibitor Sarah (Nebula) exacerbates Aβ342 phenotypes in a Drosophila model of Alzheimer's disease, The Company of Biologists Ltd., 2016, pp. 295-306."

In the Specification

Column 2, Line 17, please delete "GMIR> Aβ42" and insert -- GMR> Aβ42 --.

Signed and Sealed this
Twenty-eighth Day of March, 2023

Katherine Kelly Vidal
*Director of the United States Patent and Trademark Office*